United States Patent
Blomqvist et al.

(10) Patent No.: US 8,386,041 B2
(45) Date of Patent: Feb. 26, 2013

(54) MEDICAL DEVICE AND SYSTEM FOR DETERMINING A HEMODYNAMIC PARAMETER USING INTRACARDIAC IMPEDANCE

(75) Inventors: Andreas Blomqvist, Spånga (SE); Johan Svahn, Bromma (SE)

(73) Assignee: St. Jude Medical AB, Jarfalla (SE)

( * ) Notice: Subject to any disclaimer, the term of this patent is extended or adjusted under 35 U.S.C. 154(b) by 826 days.

(21) Appl. No.: 12/307,970

(22) PCT Filed: Jun. 21, 2006

(86) PCT No.: PCT/SE2006/000756
§ 371 (c)(1),
(2), (4) Date: Aug. 4, 2009

(87) PCT Pub. No.: WO2007/149018
PCT Pub. Date: Dec. 27, 2007

(65) Prior Publication Data
US 2010/0016915 A1    Jan. 21, 2010

(51) Int. Cl.
*A61N 1/365* (2006.01)
*A61B 5/05* (2006.01)

(52) U.S. Cl. .......................... 607/17; 600/547

(58) Field of Classification Search ............... 607/9, 17, 607/24, 28; 600/547
See application file for complete search history.

(56) References Cited

U.S. PATENT DOCUMENTS

| | | | |
|---|---|---|---|
| RE30,101 E | 9/1979 | Kubicek et al. | |
| 5,824,019 A | 10/1998 | Rueter et al. | |
| 5,843,137 A | 12/1998 | Condie et al. | |
| 6,134,472 A | 10/2000 | Strandberg et al. | |
| 6,522,914 B1 | 2/2003 | Huvelle et al. | |
| 6,567,700 B1* | 5/2003 | Turcott et al. | 607/9 |
| 2002/0138014 A1 | 9/2002 | Baura et al. | |
| 2004/0078058 A1 | 4/2004 | Holmstrom et al. | |
| 2004/0193066 A1* | 9/2004 | Carlson et al. | 600/509 |
| 2005/0215914 A1 | 9/2005 | Bornzin et al. | |

OTHER PUBLICATIONS

"The Transthoracic Impedance Cardiogrqam is a Potential Hemodynamic Sensor for an Automated External Defibrillator," Johnston et al., European Heart Journal, vol. 19 (1998) pp. 1879-1888.

* cited by examiner

*Primary Examiner* — Carl H Layno
*Assistant Examiner* — Jessica Sarcione (57) ABSTRACT

In implantable medical devices such a pacemaker or cardioverter/defibrillators (ICDs) and systems including such a device and an external programmer a measure of a hemodynamic parameter such as the cardiac output, the stroke volume, or the contractility of a patient is used to trend heart failure or in an AV/VV optimization scheme. The implantable medical device is adapted to measure the cardiac impedance and the cardiac impedance data is used to determine impedance morphology curves, which, in turn, are used to compute a measure of the hemodynamic parameter.

19 Claims, 11 Drawing Sheets

Fig. 11

MEDICAL DEVICE AND SYSTEM FOR DETERMINING A HEMODYNAMIC PARAMETER USING INTRACARDIAC IMPEDANCE

BACKGROUND OF THE INVENTION

1. Field of the Invention

The present invention generally relates to medical devices for determining a measure of hemodynamic parameters such as the cardiac output, the stroke volume, or the contractility of a patient and in particular to implantable medical devices such a pacemaker or cardioverter/defibrillators (ICDs) and systems including such a device and an external programmer for determining a measure of a hemodynamic parameter such as the cardiac output, the stroke volume, or the contractility of a patient for use, for example, in trending heart failure or in an AV/VV optimization scheme.

2. Description of the Prior Art

Intracardiac impedance variations has been found to reflect the cardiac function and may hence be utilized for heart therapy in an implantable medical device such as a heart stimulator. In particular, the cardiac impedance has been found to be of great therapeutic value since the cardiac impedance correlates well with hemodynamic parameters such as, for example, cardiac output and stroke volume.

Implantable medical devices of this above-mentioned general type is known. For example, according to United States Patent Application Publication No. 2005/0215914 the ventricular impedance is used as a measure of end-diastolic volume in order to detect heart failure. The measured impedance, which is in inverse proportion to the ventricular end-diastolic value, is compared with threshold values representative of the onset and severity of heart failure and for comparison against previously detected ventricular end-diastolic values of the patient for use in tracking the progression of heart failure over time.

United States Patent Application Publication No. 2004/0078058 describes a heart stimulator including an analyzer that analyzes at least one predetermined parameter of an average impedance morphology curve for use for the control of the stimulation. A parameter having a value that is primarily dependent on the left ventricular ejection is used. The parameter may, for example, be the integrated area below the averaged impedance morphology curve versus time, maximum or minimum value of the average impedance morphology curve, or the difference between the maximum and minimum value of the average impedance morphology curve.

U.S. Pat. No. 5,843,137 discloses a method and apparatus for automatic determination of a pacing stimulations threshold. Values such as maximum, minimum and direction values that characterize the morphology of the impedance waveform is used to discriminate between capture and loss of capture.

U.S. Pat. No. 6,134,472 describes an implantable heart stimulation device that measures electrical impedance to obtain a measure of the ventricular filling. The impedance is measured at the time when the impedance reaches a peak value, which occurs at an approximately fixed time about 250 to 300 ms after the stimulation pulse, and immediately prior to emission of a stimulation pulse. The difference between these two measurement values provides a measure of the stroke volume. This procedure requires a precise synchronization between the impedance measurements and the stimulation pulses in order to provide a measure of the stroke volume and accordingly it may be sensitive to disturbances and/or time delays.

Thus, there is a need for an improved implantable medical device and method for such a device that are capable of providing a reliable and accurate measure of hemodynamic parameters such as stroke volume, cardiac output, or contractility.

SUMMARY OF THE INVENTION

An object of the present invention is to provide an improved implantable medical device and method for such a device that are capable of providing a reliable and accurate measure of hemodynamic parameters such as stroke volume, cardiac output, or contractility.

Another object of the present invention is to provide a system including an implantable medical device and an external programmer apparatus that is capable of providing a reliable and accurate measure of hemodynamic parameters such as stroke volume, cardiac output, or contractility.

A further object of the present invention is to provide an implantable medical device and a system including an implantable medical device and an external programmer apparatus that are capable of providing a reliable and accurate measure of hemodynamic parameters such as stroke volume, cardiac output, or contractility for use in optimizing settings of the implantable device, for example, pacing parameters or for deriving a condition or change of a condition of a patient.

According to an aspect of the present invention, there is provided an implantable medical device including a pulse generator adapted to produce cardiac stimulating pacing pulses, the device being connectable to at least one lead comprising electrodes for delivering the pulses to cardiac tissue of a heart of a patient. The implantable medical device includes an impedance measuring unit connectable to at least two electrodes adapted to measure cardiac impedance of the heart, the impedance measuring unit being adapted to provide impedance information corresponding to the measured impedance; an impedance morphology determining unit adapted to receive the impedance information and to determine an impedance morphology curve from the impedance information; and a calculation unit adapted to detect an extreme point section of the impedance morphology curve and to calculate a measure of a hemodynamic parameter of the heart utilizing the extreme point section.

According to a second aspect of the present invention, there is provided a medical system including an external programmer apparatus comprising a communication unit and an implantable medical device including a pulse generator adapted to produce cardiac stimulating pacing pulses, the implantable device being connectable to at least one lead comprising electrodes for delivering the pulses to cardiac tissue of a heart of a patient, and a communication unit, wherein the external apparatus and the implantable device are adapted for two-way communication of data using the communication units. The implantable medical device further has an impedance measuring unit connectable to at least two electrodes adapted to measure cardiac impedance of the heart, the impedance measuring unit being adapted to provide impedance information corresponding to the measured impedance. The external apparatus is adapted to obtain the impedance information via the communication unit and further comprises an impedance morphology determining unit adapted to receive the impedance information and to determine an impedance morphology curve from the impedance information; and a calculation unit adapted to detect an extreme point section of the impedance morphology curve and to calculate a measure of a hemodynamic parameter of the heart utilizing the extreme point section.

According to a third aspect of the present invention, there is provided a medical system including an external programmer apparatus having a communication unit and an implantable medical device including a pulse generator adapted to produce cardiac stimulating pacing pulses, the implantable device being connectable to at least one lead comprising electrodes for delivering the pulses to cardiac tissue of a heart of a patient, and a communication unit, wherein the external apparatus and the implantable device are adapted for two-way communication of data using the communication units. The implantable medical device further has an impedance measuring unit connectable to at least two electrodes adapted to measure cardiac impedance of the heart, the impedance measuring unit being adapted to provide impedance information corresponding to the measured impedance; and an impedance morphology determining unit adapted to receive the impedance information and to determine an impedance morphology curve from the impedance information. The external apparatus is adapted to obtain the impedance morphology curve via the communication unit and further has a calculation unit adapted to detect an extreme point section of the impedance morphology curve and to calculate a measure of a hemodynamic parameter of the heart utilizing the extreme point section.

Thus, the present invention is based on the insight that the intracardiac impedance variations reflect the cardiac function and hence can be utilized for heart therapy in an implantable medical device such as a heart stimulator and that the cardiac impedance has been found to be of great therapeutic value since the cardiac impedance correlates very well with hemodynamic parameters such as, for example, cardiac output and stroke volume. In particular, the actual shape of the cardiac impedance signal and the morphology of the peak section and its immediate surroundings has been found to contain valuable information regarding the hemodynamic performance of a patient. This information is, according to the present invention, used to determine or calculate a measure of a hemodynamic parameter of the patient, for example, cardiac output, stroke volume, or contractility. This measure may, in turn, be used to control heart stimulation to optimize hemodynamics or to trend, for example, the development of heart failure.

According to the second aspect of the present invention, the programmer obtains impedance data from the implantable device and performs the impedance morphology determination and the calculation of the hemodynamic measure. That is, the impedance data processing is mainly performed in the programmer and thus the data processing executed in the implantable device can be minimized. The impedance data transfer to the programmer may be performed continuously or at regular intervals.

According to the third aspect of the present invention, the programmer obtains impedance curves from the implantable device and performs the calculation of the hemodynamic measure. That is, the calculation of the hemodynamic measure is performed in the programmer and thus the data processing executed in the implantable device can be reduced. The transfer of impedance curves to the programmer may be performed continuously or at regular intervals.

In one embodiment of the present invention, the implantable medical device includes an analyzer adapted to analyze the measure to optimize at least one pacing parameter of the pulse generator or to derive a change of a condition of the patient. Thereby, the heart stimulation pulses may be controlled such that the patient hemodynamics is optimized. For example, an AV/VV interval may be optimized. The obtained measure can also be used to trend conditions such as, for example, heart failure. In an alternative embodiment, the analyzer is arranged in the external programmer apparatus.

According another embodiment of the present invention, the calculation unit is adapted to calculate the measure by means of the shape of the impedance morphology curve in a time window surrounding the peak section of the impedance morphology curve.

In a further embodiment of the present invention, the impedance morphology determining unit is adapted to determine an averaged impedance morphology curve from the impedance information during a time interval of a number of cardiac cycles of the heart. For example, a predetermined number of consecutive heart beats may be used to create the averaged impedance curve. In an alternative embodiment, the impedance morphology determining unit is adapted to perform a filtering procedure of the received impedance information and to determine an impedance morphology curve from the filtered impedance information.

In another embodiment of the present invention, the calculation unit is adapted to detect the maximum value of the impedance morphology curve and to centre the time window about the value. The maximum value or peak section of the curve may be located by using the first and second time derivatives of the curve section.

In yet another embodiment of the present invention, the calculation unit is adapted to fit a polynomial of degree two to the section of the impedance morphology curve in the time window.

According to further embodiment of the present invention, a curvature component of the polynomial is used as the measure. The second degree constant has been found to contain information of the magnitude of the curvature of the cardiac impedance waveform and may thus be used as the measure of the shape of the cardiac impedance signal, and, in turn, as a measure of the hemodynamic parameter, for example, the stroke volume or the cardiac output.

In another embodiment of the procedure for calculating the measure according to the present invention, the sample corresponding to the maximum value is identified, a window centered about the maximum value containing a predetermined number of samples is defined, the values of the start and end samples of the window, respectively, are identified, an average value of the start and end values is calculated, and a ratio of the average value and the maximum value is calculated as the measure. According to an alternative, a window centered about the maximum value having a predetermined length of time is defined and the samples corresponding to the start and end of the time window are identified and used to calculate the ratio.

Alternatively, to calculate the measure of the hemodynamic parameter, the sample corresponding to the maximum value is identified, a window centered about the maximum value containing a predetermined number of samples is defined, and an area of the window by adding the values of the predetermined number of samples is calculated as the measure. According to an alternative, a window centered about the maximum value having a predetermined length of time is defined and the values of the samples included in the time window are added up to calculate the area.

In a further embodiment of the procedure for calculating the measure in accordance with the present invention, the sample corresponding to the maximum value is identified, a time window centered about the maximum value containing a predetermined number of samples is defined, the values of the start and end values of the window, respectively, are identified, a first average slope from the sample corresponding to the start value to the sample corresponding to the maximum value is calculated, a second average slope from the sample corresponding to the maximum value to the sample corresponding to the end value is calculated, and the first slope and the second slope is used to calculate the measure. For example, a ratio between the slopes or a product of the slopes can be calculated.

In yet another embodiment of the present invention, a time window is defined at a predetermined amplitude in relation to the maximum value and a width of the time window as the measure is calculated.

In one embodiment, the resistive part of the cardiac impedance is used. Furthermore, the impedance information may also or alternatively, for example, include the magnitude of the complex impedance, the real and/or imaginary part (i.e. the inductive or capacitive part) of the complex impedance.

According to further embodiments, the hemodynamic parameter is stroke volume, cardiac output, or contractility.

In an embodiment, the implantable medical device may a posture sensor adapted to sense at least one predetermined posture of the patient and to provide at least one posture indicating signal. A cardiac impedance measuring session may be initiated upon an indication that the patient is in at least one predetermined posture. Alternatively, the implantable medical may comprise a breathing rate sensor adapted to sense a breathing rate of the patient and to provide at least one breathing rate indicating signal. A cardiac impedance measuring session may be initiated upon an indication of a breathing rate within at least one predetermined interval. In a further example, the implantable medical device may include an activity level sensor adapted to sense an activity level of the patient and to provide at least one activity level indicating signal. In this case, a cardiac impedance measuring session may be initiated upon indication of an activity level within at least one predetermined interval. As the skilled person realizes, one or several of the above-mentioned criteria may be combined. Moreover, other criteria may also be conceivable, for example, the heart rate of the patient. By only performing the cardiac impedance measurements under certain conditions, e.g. at a specific body posture, the reliability and accuracy of the impedance data, and thereby of the measure of the hemodynamic, can be improved since the measurements are performed under reproducible conditions.

The features that characterize the invention, both as to organization and to method of operation, together with further objects and advantages thereof, will be better understood from the following description used in conjunction with the accompanying drawings. It is to be expressly understood that the drawings is for the purpose of illustration and description and is not intended as a definition of the limits of the invention. These and other objects attained, and advantages offered, by the present invention will become more fully apparent as the description that now follows is read in conjunction with the accompanying drawings.

DESCRIPTION OF THE PREFERRED EMBODIMENTS

Figure 1:
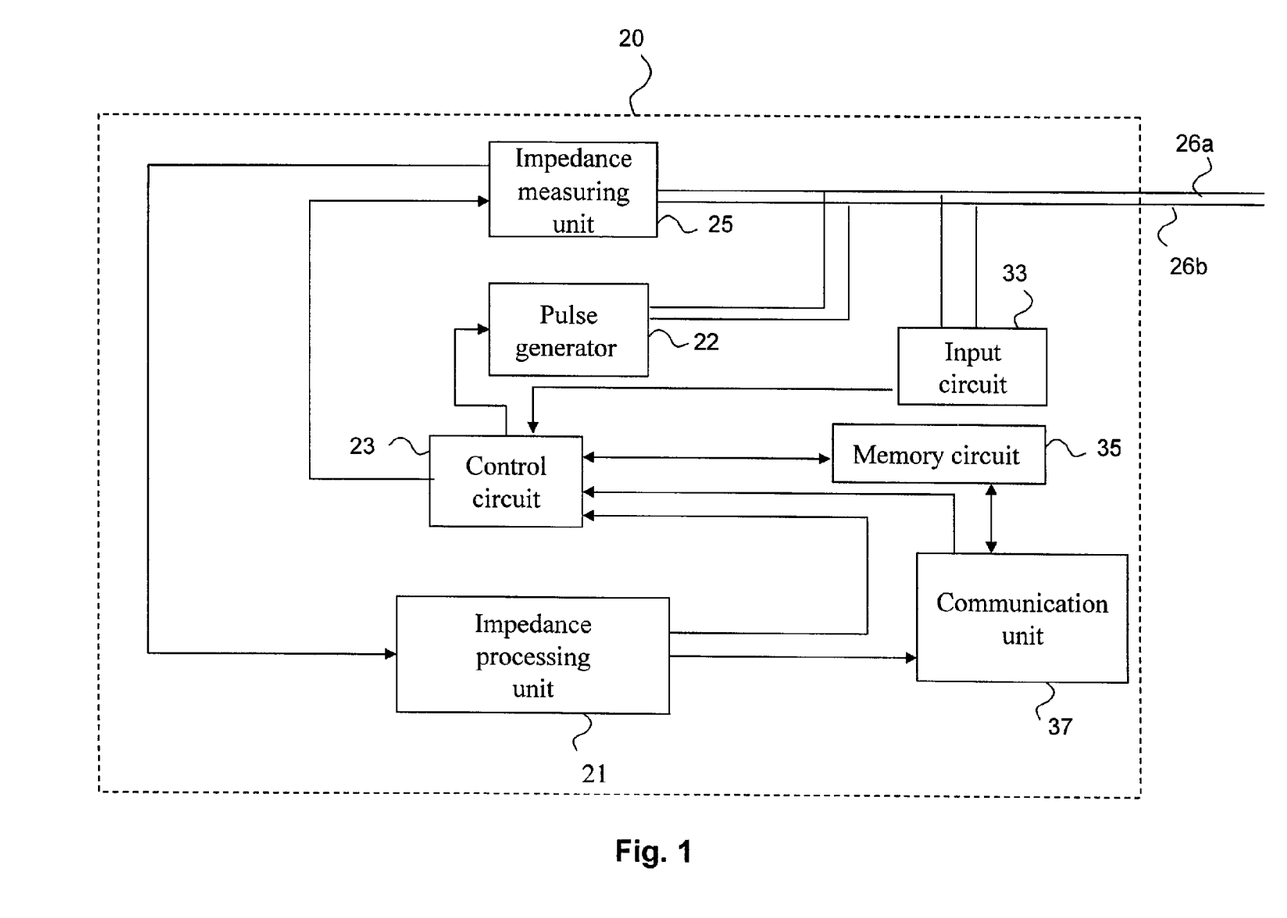
FIG. 1 is block diagram of the primary functional components of an embodiment of the implantable medical device according to the present invention.

With reference first to FIG. 1, an embodiment of the implantable medical device according to the present invention will be shown. This embodiment of the present invention is implemented in the context of a pacemaker 20 implanted in a patient (not shown). The pacemaker 20 has a housing being hermetically sealed and biologically inert. Normally, the housing is conductive and may, thus, serve as an electrode. One or more pacemaker leads, where only two are shown in FIGS. 1, 26a and 26b, are electrically coupled to the pacemaker 20 in a conventional manner. The leads 26a, 26b extend into the heart (not shown) via a vein of the patient. One or more conductive electrodes for receiving electrical cardiac signals and/or for delivering electrical pacing to the heart are arranged near the distal ends of the leads 26a, 26b. As the skilled man in the art realizes, the leads 26a, 26b may be implanted with its distal end located in either the atrium or ventricle of the heart.

The leads 26a, 26b may be unipolar or bipolar, and may include any of the passive or active fixation means known in the art for fixation of the lead to the cardiac tissue. For example, a good fixation of electrodes can be obtained by means of a screw-in electrodes. Alternatively, the lead distal tip (not shown) may include a tined tip or a fixation helix.

The leads 26a, 26b comprises one or more electrodes, such a tip electrode or a ring electrode, arranged to, inter alia, transmit pacing pulses for causing depolarization of cardiac tissue adjacent to the electrode(-s) generated by a pace pulse generator 22 under influence of a control circuit 23 comprising a microprocessor. The control circuit 23 controls, inter alia, pace pulse parameters such as output voltage and pulse duration. A memory circuit 31 is connected to the control circuit 27, which memory circuit 35 may include a random access memory (RAM) and/or a non-volatile memory such as a read-only memory (ROM). Detected signals from the patient's heart are processed in an input circuit 33 and are forwarded to the microprocessor of the control circuit 27 for use in logic timing determination in known manner.

Furthermore, an impedance measuring unit 25 is adapted to carry out impedance measurements of the cardiac impedance of the patient. The impedance vector used should preferably capture the filling and emptying of the ventricle (right or left). The impedance measuring unit 25 is thus arranged to apply excitation current pulses between a first electrode and a second electrode arranged to positioned, for example, within a heart of the patient. In one embodiment, the current is emitted between a right ventricular tip electrode and a left ventricular tip electrode. The first and second electrode may also be positioned outside the heart. The impedance measuring unit 25 is also arranged to measure the voltage between a third and fourth electrode arranged, for example, at a lead 26a, or 26b. The third and fourth electrode are arranged such that they can be located within the heart of the patient, for example, in a vein/artery of the heart. In one embodiment, the voltage is sensed between a right ventricular ring electrode and a left ventricular ring electrode.

According to another embodiment, tri-polar measurements are used to perform the impedance measurements where the current is sent out between an RV-tip (i.e. the distal electrode in a bipolar lead located in right ventricle) and an RV-coil (i.e. the conductor in a bipolar lead having a helical configuration located in the right ventricle) and the voltage is measured between an RV-ring (i.e. the proximal electrode in a bipolar lead located in right ventricle) and the RV-coil.

The impedance measuring unit 25 may comprise an amplifier (not shown) that amplifies the evoked voltage response, i.e. the measured voltage, and may be synchronized in a multiplier with the excitation current. Thus, the impedance measuring unit 25 obtains the cardiac impedance given by the delivered current and the evoked voltage response. Then, the impedance information corresponding to the measured impedance is sent to an impedance processing unit 21.

The impedance information used may include the resistive part of the cardiac impedance. Furthermore, the impedance information may also or alternatively, for example, include the magnitude of the complex impedance, the real and/or imaginary part (i.e. the inductive or capacitive part) of the complex impedance.

The impedance processing unit 21 may be adapted to determine an averaged impedance morphology curve from the received impedance information during a time interval of a plurality of cardiac cycles. In another embodiment, the received impedance information is filtered and a morphology curve based on the impedance information obtained during one heart beat is determined. The signals may be bandpass filtered to remove the DC-component. Furthermore, an extreme point section of the impedance morphology curve is detected and a measure of a hemodynamic parameter of the heart, for example, stroke volume, cardiac output, or contractility, utilizing the extreme point section is calculated. In one embodiment, the extreme point section is a peak section. Different approaches for calculating the measure will be discussed below. Thereafter, the obtained measure is analyzed to optimize at least one pacing parameter of the pulse generator or to derive a change of a condition of the patient. The control circuit 23 may be connected to the impedance processing unit 21 to control the heart stimulation pulse generator 22 in response to the output from the impedance processing unit 21 such that the patient hemodynamics can be optimized. For example, an AV/VV interval may be optimized. The obtained measure can also be used to trend, for example, heart failure.

Figure 2:
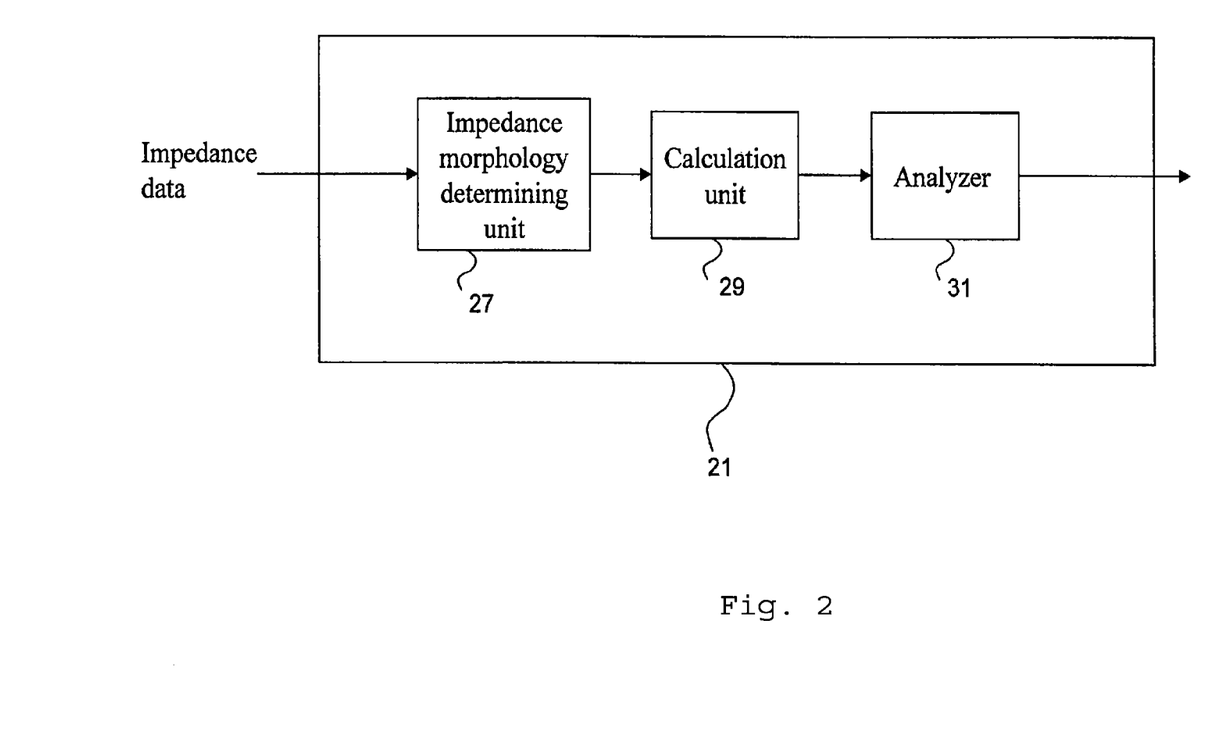
FIG. 2 is a block diagram of a part of the embodiment of the implantable medical device shown in FIG. 1.

With reference to FIG. 2, an embodiment of the impedance processing unit 21 will be described. An impedance morphology determining unit 27 is adapted to receive the impedance information corresponding to the measured impedance from the impedance measuring unit 25. The impedance morphology determining unit 27 may be adapted to determine an averaged impedance morphology curve from the received impedance information during a time interval of a plurality of cardiac cycles. In another embodiment, the received impedance information is median filtered and a morphology curve based on the impedance signal obtained during one heart beat is determined.

In a calculation unit 29, an extreme point section of the impedance morphology curve is detected and a measure of a hemodynamic parameter of the heart, for example, stroke volume, cardiac output, or contractility, utilizing the extreme point section is calculated. In one embodiment, the extreme point section is a peak section. The measure obtained from the calculation unit 29 is analyzed in an analyzer 31 to optimize at least one pacing parameter of the pulse generator or to derive a change of a condition of the patient. The control circuit 23 may be connected to the analyzer 31 for the optimization discussed above.

The implantable medical device 20 is powered by a battery (not shown), which supplies electrical power to all electrical active components of the medical device 20. Data contained in, for example, the memory circuit 35 can be transferred to a programmer (not shown in FIG. 1) via a communication unit 37, e.g. a telemetry unit, including a programmer interface for use in analyzing system conditions, patient information, etc. The analyzer 31 may also transfer data to the programmer via the communication unit 37.

Furthermore, the implantable medical device according to the present invention may comprise a posture detecting sensor (not shown) arranged to detect, for example, a predetermined, specific body posture of the patient. The posture detecting sensor may be connected to the control circuit and adapted to provide at least one posture indicating signal. In one embodiment, the impedance measuring unit is adapted to initiate an impedance measuring session upon receiving a posture indicating signal that indicates that the patient is in at least one predetermined posture. For example, the impedance measuring session may be initiated when the patient is lying on the back.

In another embodiment, the implantable medical device may comprise a breathing rate sensor (not shown) adapted to sense a breathing rate of the patient. The breathing rate sensor may be connected to the control circuit and is adapted to provide at least one breathing rate indicating signal. The impedance measuring unit may be adapted to initiate a cardiac impedance measuring session upon receiving a breathing rate indicating signal that indicates a breathing rate within at least one predetermined interval. For example, the impedance measuring session may be initiated when the breathing rate is below a certain level.

In yet another embodiment, the implantable medical device may comprise an activity level sensor (not shown) adapted to sense an activity level of the patient. The activity level sensor may be connected to the control circuit and is adapted to provide at least one activity level indicating signal. The impedance measuring unit may be adapted to initiate a cardiac impedance measuring session upon receiving an activity level signal indicating signal that indicates an activity level within at least one predetermined interval.

As the skilled person realizes, one or several of the above-mentioned criteria may be combined. Moreover, other criteria may also be conceivable, for example, the heart rate of the patient. By only performing the cardiac impedance measurements under certain conditions, e.g. at a specific body posture, the reliability and accuracy of the impedance data, and thereby of the measure of the hemodynamic, can be improved since the measurements are performed under reproducible conditions.

Figure 3:
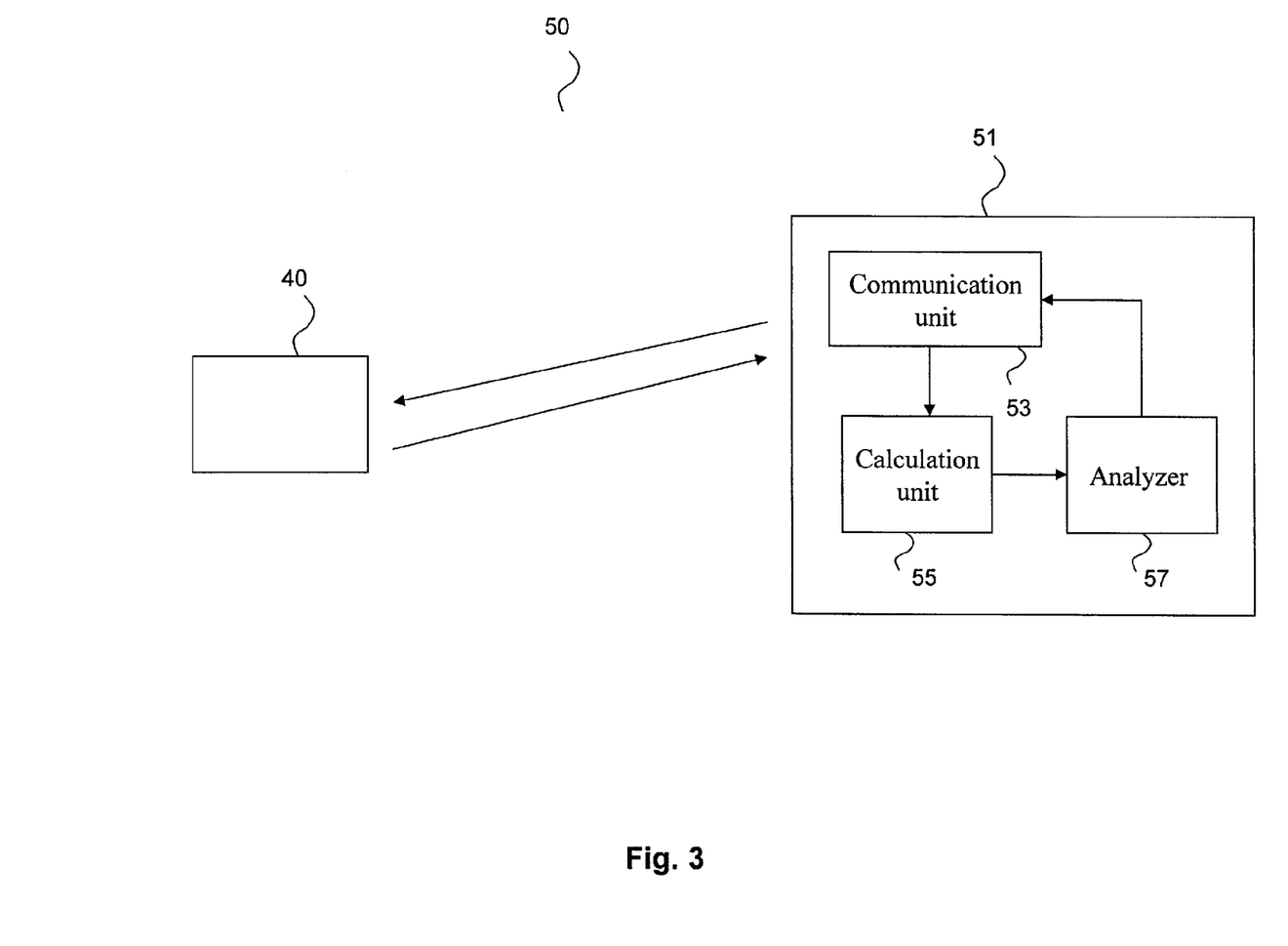
FIG. 3 is a general block diagram of an embodiment of the system according to the present invention.
Figure 4:
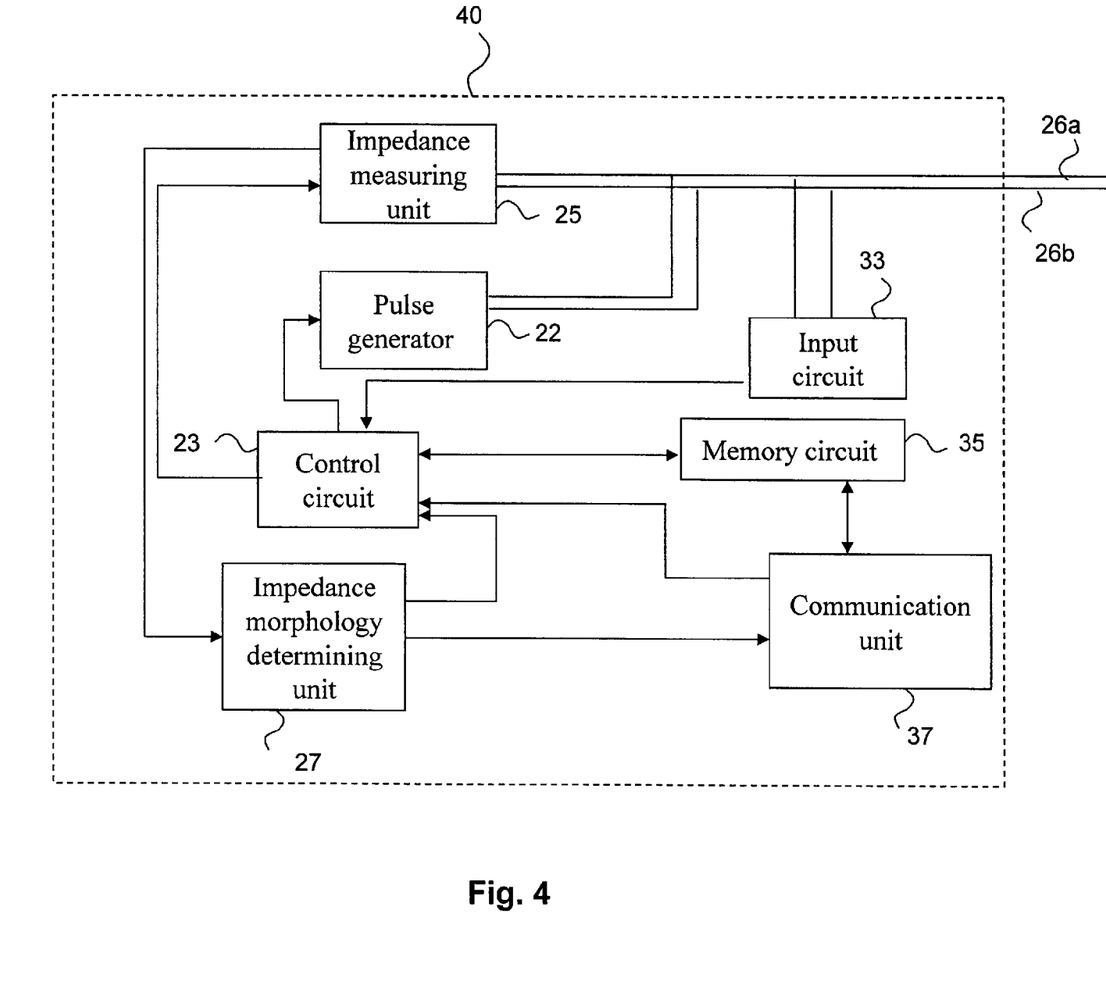
FIG. 4 is block diagram of the primary functional components of an embodiment of the implantable medical device of the system shown in FIG. 4 according to the present invention.
Figure 5:
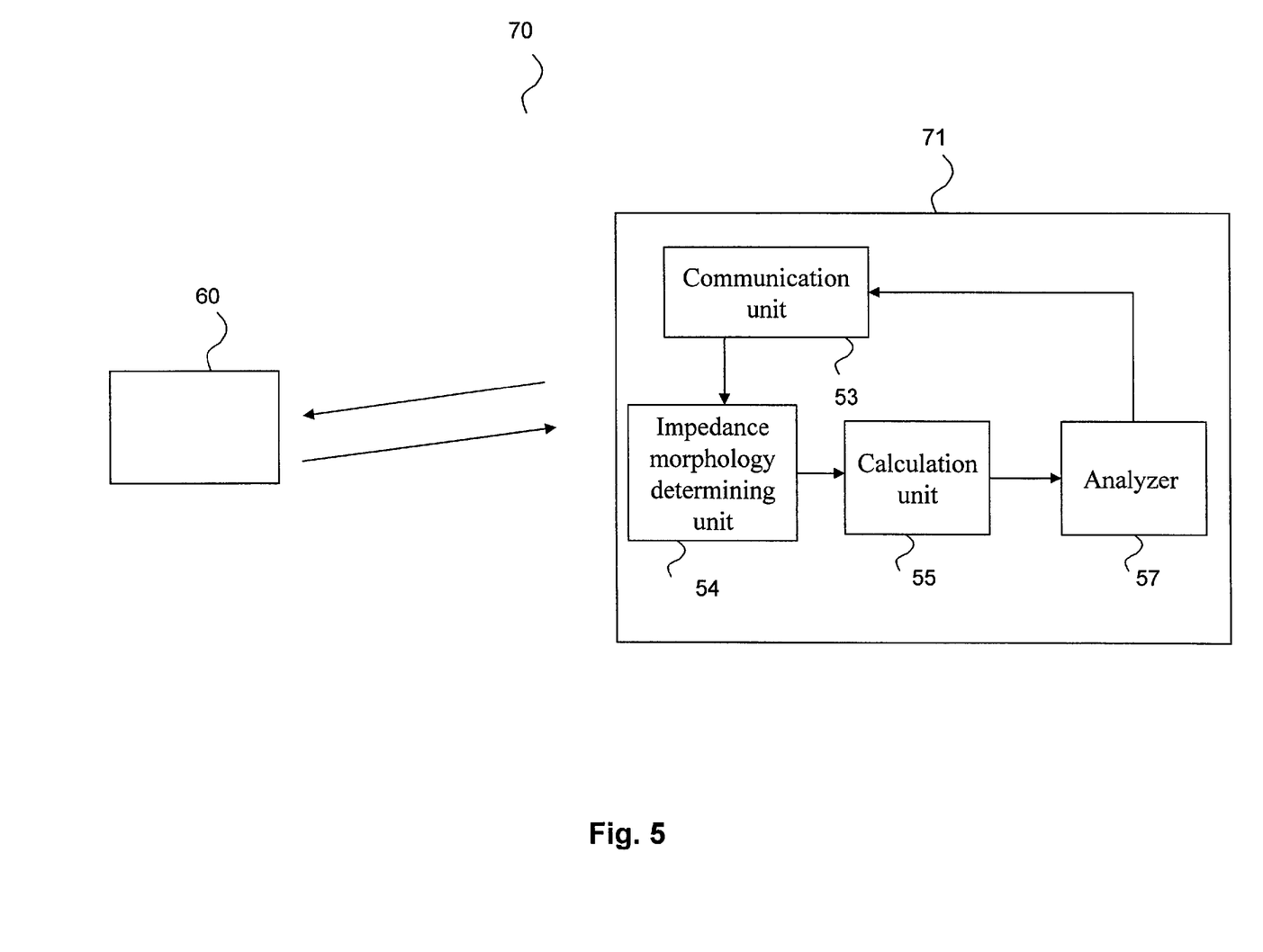
FIG. 5 is a general block diagram of another embodiment of the system according to the present invention.
Figure 6:
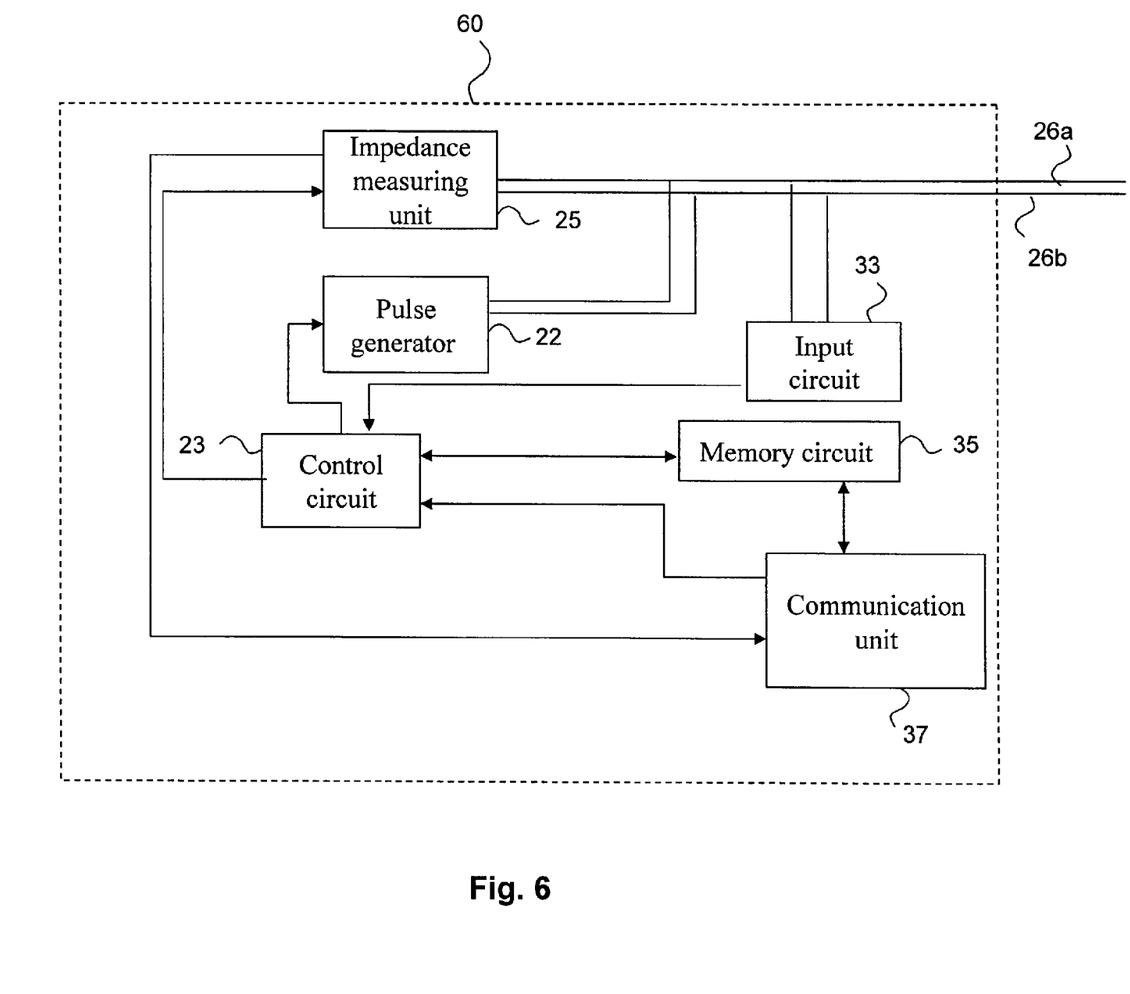
FIG. 6 is block diagram of the primary functional components of an embodiment of the implantable medical device of the system shown in FIG. 5 according to the present invention.

With reference now to FIGS. 3-6, embodiments of the system according to the present invention will be discussed. Like or similar parts in FIGS. 1, 2, 4 and 6 are denoted with the same reference numerals and therefore the description of such parts will omitted since they were discussed above with respect to FIGS. 1 and 2. Likewise, like or similar parts in FIGS. 3 and 5 are denoted with the same reference numerals and therefore the description of such parts will omitted since they were discussed above with respect to FIG. 3.

With reference first to FIGS. 3 and 4, one embodiment of the system according to the present invention will be described. In FIG. 3, it can be seen that the system 50 includes an implantable medical device 40, which is shown in more detail in FIG. 4, and an external programmer apparatus 51. The implantable device 40 and the external programmer 51 are adapted for two-way communication of data between each other via communication units 37 and 53, respectively. In this embodiment, the implantable medical device 40 comprises the impedance morphology determining unit 27 adapted to receive the impedance information from the impedance measuring unit 25 and to determine an impedance morphology curve from the impedance information. The impedance morphology curves can be stored in the memory circuit 37 or they may be buffered locally in the impedance morphology determining unit 27 before being transferred to the external programmer apparatus 51 via the communication units 37 and 53, respectively. This data transfer can be performed either continuously or at predetermined intervals of time. In the external programmer apparatus 51, the received impedance morphology data is processed in a calculation unit 55 to detect an extreme point section of the impedance morphology curve (or extreme points sections of respective curves) and a measure of a hemodynamic parameter of the heart, for example, stroke volume, cardiac output, or contractility, utilizing the extreme point section is calculated using the extreme point section. In one embodiment, the extreme point section is a peak section. The measure obtained from the calculation unit 55 may be analyzed in an analyzer 57 to optimize at least one pacing parameter of the pulse generator of the implantable medical device 40 or to derive a change of a condition of the patient. The updated pacing parameters may be communicated to the implantable medical device 40 via the communication units 53 and 37, respectively, to control the heart stimulation pulse generator 22 in response to the output from the impedance processing unit 57 such that the patient hemodynamics can be optimized. For example, an AV/VV interval may be optimized. The obtained measure can also be used to trend, for example, heart failure.

With reference first to FIGS. 5 and 6, another embodiment of the system according to the present invention will be described. In FIG. 5, it can be seen that the system 70 includes an implantable medical device 60, which is shown in more detail in FIG. 6, and an external programmer apparatus 71. The implantable device 60 and the external programmer 71 are adapted for two-way communication of data between each other via communication units 37 and 53, respectively. In this embodiment, the impedance information data from the impedance measuring unit 25 is streamed to the external programmer apparatus 71. Alternatively, the impedance information data can be stored in the memory circuit 37 or buffered locally in the impedance measuring unit 25 before being transferred to the external programmer apparatus 71 via the communication units 37 and 53, respectively. This data transfer can be performed at predetermined intervals of time. In the external programmer apparatus 71, the received impedance data is processed in a impedance morphology determination unit 54 to determine an averaged impedance morphology curve from the received impedance information during a time interval of a plurality of cardiac cycles. In another embodiment, the received impedance information filtered and a morphology curve based on the impedance signal obtained during one heart beat is determined. In the calculation unit 55 an extreme point section of the impedance morphology curve (or extreme points sections of respective curves) and a measure of a hemodynamic parameter of the heart, for example, stroke volume, cardiac output, or contractility, utilizing the extreme point section is calculated using the extreme point section. In one embodiment, the extreme point section is a peak section. The measure obtained from the calculation unit 55 may be analyzed in an analyzer 57 to optimize at least one pacing parameter of the pulse generator of the implantable medical device 60 or to derive a change of a condition of the patient. The updated pacing parameters may be communicated to the implantable medical device 60 via the communication units 53 and 37, respectively, to control the heart stimulation pulse generator 22 in response to the output from the impedance processing unit 57 such that the patient hemodynamics can be optimized. For example, an AV/VV interval may be optimized. The obtained measure can also be used to trend, for example, heart failure.

Figure 7:
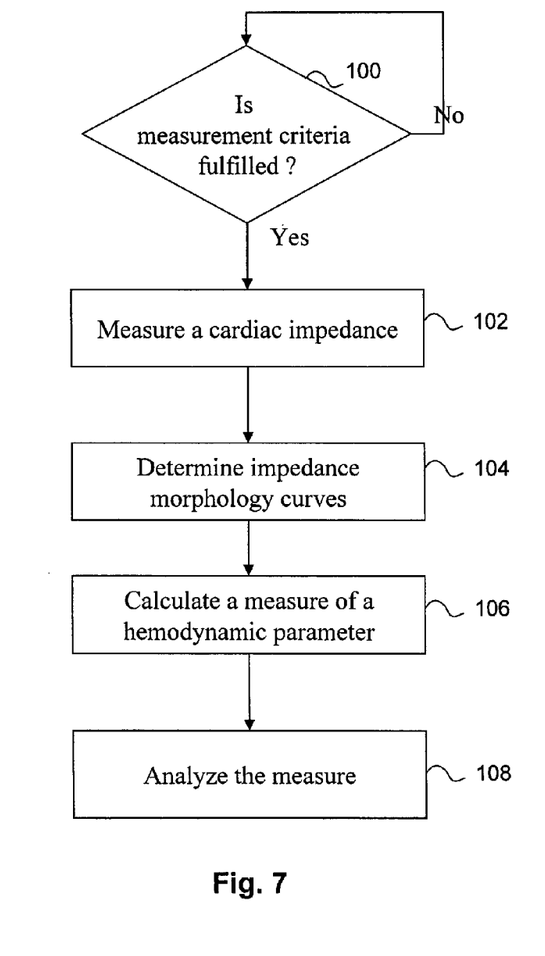
FIG. 7 is a flow chart illustrating the steps in accordance with one embodiment of the present invention for determining a measure of a hemodynamic parameter.

Turning now to FIG. 7, a general description of the method for calculating the measure of a hemodynamic parameter according to the present invention will be given. First, at step 100, it may be checked whether at least one predetermined measurement criteria is fulfilled, for example, whether the patient is in a predetermined body posture or whether an breathing rate is within a predetermined interval. However, this step is optional. At step 102, impedance measurements of the cardiac impedance of the patient is performed. If the criteria check step is performed, the measurement step 102 is performed if the predetermined criteria is fulfilled. Thereafter, at step 104, an averaged impedance morphology curve from the received impedance information during a time interval of a plurality of cardiac cycles is determined. In another embodiment, the received impedance information is filtered and a morphology curve based on the impedance signal obtain during one heart beat is determined. As discussed above, this step may be performed either in the implantable medical device or in the external programmer apparatus. If the morphology curves are calculated in the programmer, the impedance data may streamed over to the programmer from the implantable device or is may be transferred at regular intervals. If the curves are calculated in the implantable device, the curves may be transferred on a continuous basis or at regular intervals. Then, at step 106, an extreme point section of the impedance morphology curve is detected. In one embodiment, the extreme point section is a peak section. A measure of a hemodynamic parameter of the heart, for example, stroke volume, cardiac output, or contractility, utilizing the extreme point section is calculated. Different approaches for calculating the measure will be discussed below. The calculation step may be executed in the programmer or in the implantable device.

Thereafter, at step 108, the obtained measure may be analyzed to optimize at least one pacing parameter of the pulse generator or to derive a change of a condition of the patient. The control circuit 23 may receive the updated pacing parameters to control the heart stimulation pulse generator 22 in response to the output from the such that the patient hemodynamics can be optimized. For example, an AV/VV interval may be optimized. The obtained measure can also be used to trend, for example, heart failure.

Referring now to FIGS. 8-12, different calculations procedures for calculating the measure of a hemodynamic parameter of the heart, for example, stroke volume, cardiac output, or contractility according to the present invention will be described. As discussed above, the actual shape of the cardiac impedance signal and especially the morphology of the extreme points sections, e.g. the peak point section, and the immediate surroundings contain information of the hemodynamic status of the patient that can be used to obtain the above-mentioned relative measure of the hemodynamic parameter.

Figure 8:
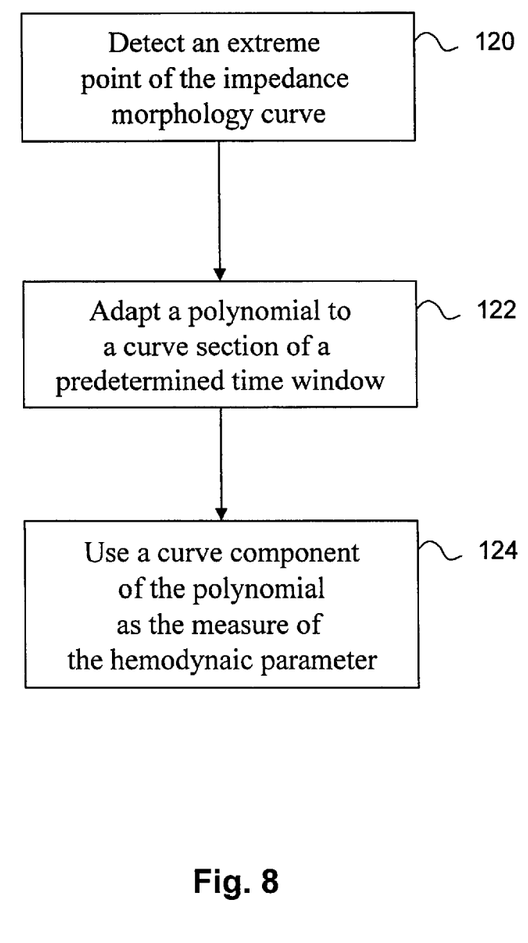
FIG. 8 is a flow chart of an embodiment of the calculation procedure according to the present invention.

With reference first to FIG. 8, a first embodiment of the calculation procedure according to the present invention will be discussed. First, at step 120, an extreme point of the impedance morphology curve is detected. In this embodiment, a top part or peak value of the impedance morphology curve is detected and time window having a predetermined length is centered about this peak value. To locate the peak section of the curve, minima and maxima in the first and second time derivative of the curve can be used. Thereafter, at step 122, a polynomial of a predetermined degree, e.g. a $2^{nd}$ degree polynomial, is adapted to the curve section of the predetermined time window. If the $2^{nd}$ degree polynomial is used, it will hence be the following form: $a \cdot x^2 + b \cdot x + c$. Then, at step 124, the constant a is stored as a measure of the curvature of the waveform peak and is used as a measure of the hemodynamic parameter.

Figure 9:
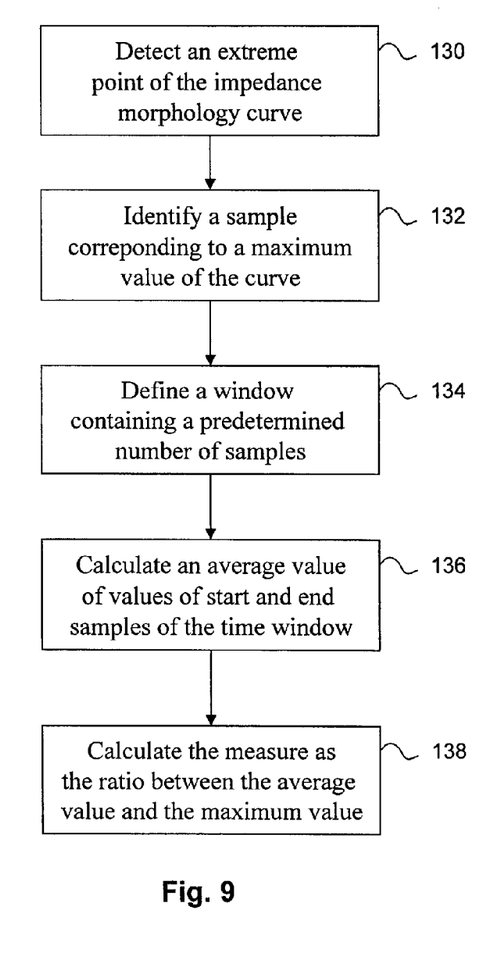
FIG. 9 is a flow chart of another embodiment of the calculation procedure according to the present invention.

Turning instead to FIG. 9, another embodiment of the calculation procedure according to the present invention will be discussed. First, at step 130, an extreme point of the impedance morphology curve is detected. In this embodiment, a top part or peak value of the impedance morphology curve is detected and time window having a predetermined length is centered about this peak value. Then, at step 132, the sample, $S_n$, corresponding to the maximum value or peak value is identified. Subsequently, at step 134, a window consisting of samples $S_{n-m}$ to $S_{n+m}$ centered about the maximum value containing a predetermined number 2 m+1 of samples, wherein m may be a number between 5 and 35 with $f_s$=128 Hz (corresponding to 40-280 mS). Thereafter, at step 136, the values of the start and end points or samples of the window, respectively, are identified and an average value of the start and end values are calculated in accordance with:

$$\frac{\text{Value\_}S_{n+m} + \text{Value\_}S_{n-m}}{2} = \alpha$$

Then, at step 138, a measure of the hemodynamic parameter is calculated as a ratio of the average value and the maximum value β in accordance with:

$$\text{Measure of hemodynamic parameter} = \frac{\alpha}{\beta}$$

Figure 10:
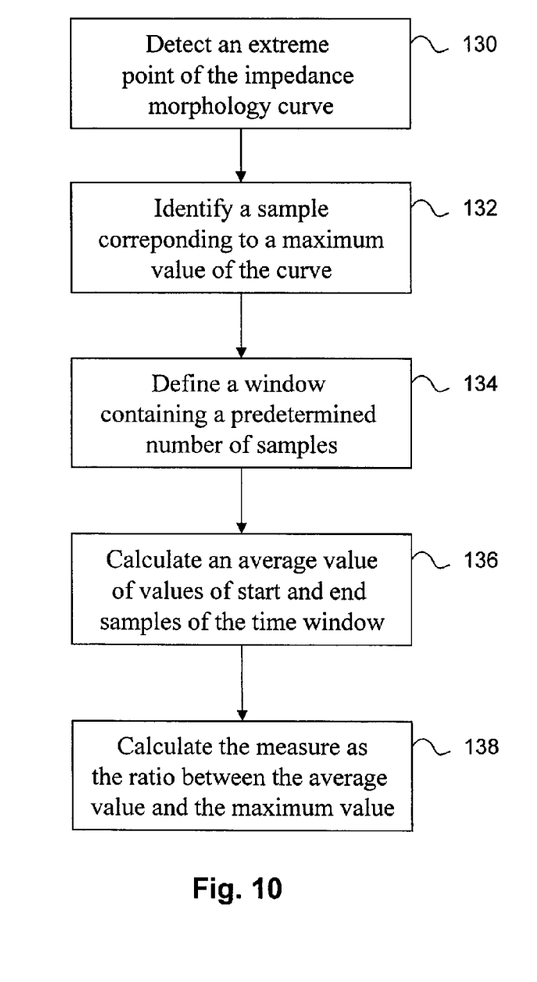
FIG. 10 is a flow chart of yet another embodiment of the calculation procedure according to the present invention.

With reference now to FIG. 10, a further embodiment of the calculation procedure according to the present invention will be discussed. First, at step 140, an extreme point of the impedance morphology curve is detected. In this embodiment, a top part or peak value of the impedance morphology curve is detected and a time window having a predetermined length is centered about this peak value. Then, at step 142, the sample $S_n$, corresponding to the maximum value or peak value is identified. Subsequently, at step 144, a window consisting of samples $S_{n-m}$ to $S_{n+m}$ centered about the maximum value containing a predetermined number 2 m+1 of samples, wherein m may be a number between 5 and 35 with $f_s$=128 Hz (corresponding to 40-280 mS). Thereafter, at step 146, the area of the defined curve section is estimated by adding up sample values for the samples $S_{n-m}$ to $S_{n+m}$. This can be performed with or without time- or amplitude normalization.

Finally, at step 148, the calculated area is used a the measure of the hemodynamic parameter, for example, cardiac output or stroke volume.

Figure 11:
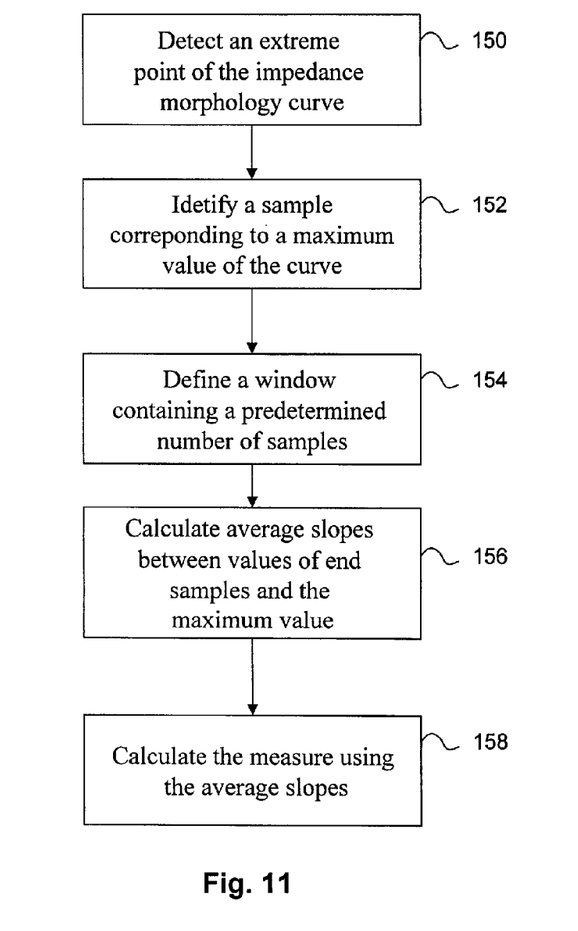
FIG. 11 is a flow chart of a further embodiment of the calculation procedure according to the present invention.

Turning to FIG. 11, yet another embodiment of the calculation procedure according to the present invention will be discussed. First, at step 150, an extreme point of the impedance morphology curve is detected. In this embodiment, a top part or peak value of the impedance morphology curve is detected and time window having a predetermined length is centered about this peak value. Then, at step 152, the sample $S_n$, corresponding to the maximum value or peak value is identified. Subsequently, at step 154, a window consisting of samples $S_{n-m}$ to $S_{n+m}$ centered about the maximum value containing a predetermined number 2 m+1 of samples, wherein m may be a number between 5 and 35 with $f_s$=128 Hz (corresponding to 40-280 mS). Thereafter, at step 156, the average slopes from sample $S_{n-m}$ to the maximum point, A, and from the maximum point to the sample $S_{n+m}$, are calculated, respectively. Finally, at step 158, the measure is calculated as the ratio between the slopes in accordance with the following:

$$\text{Measure of hemodynamic parameter} = \frac{A}{-B}.$$

This ratio thus describes a warpedness of the section of the curve of the window.

Alternatively, the measure can be calculated as:

Measure of hemodynamic parameter=$A \cdot (-B)$.

According to a further alternative, the measure is calculated as:

$$\text{Measure of hemodynamic parameter} = \frac{1}{A + (-B)}.$$

According to still another embodiment, a time window at a predetermined amplitude in relation to the maximum value is defined and a width of the time window is calculated as the measure.

Although modifications and changes may be suggested by those skilled in the art, it is the intention of the inventors to embody within the patent warranted heron all changes and modifications as reasonably and properly come within the scope of their contribution to the art.

The invention claimed is:

1. An implantable medical device comprising:
    a pulse generator that emits cardiac stimulating pacing pulses;
    at least one lead comprising electrodes configured to deliver said pulses to cardiac tissue of a heart of a patient;
    an impedance measuring unit connectable to at least two electrodes to measure cardiac impedance of said heart, said impedance measuring unit generating impedance information corresponding to said measured impedance;
    an impedance morphology determining unit that receives said impedance information and determines an impedance morphology curve from said impedance information; and
    a calculation unit that detects an extreme point section of said impedance morphology curve and fits a second degree polynomial to the section of the impedance morphology curve in a time window surrounding said extreme point section of said impedance morphology curve and calculates a measure of a hemodynamic parameter of said heart as a function of a curvature component of the polynomial, and that makes said measure available as an output signal.

2. The implantable medical device according to claim 1, wherein said calculation unit detects a peak section as said extreme point section.

3. The implantable medical device according to claim 2, wherein said calculation unit calculates said measure by means of the shape of the impedance morphology curve in a time window surrounding said peak section of said impedance morphology curve.

4. The implantable medical device according to claim 3, wherein said calculation unit detects the maximum value of said impedance morphology curve and to center said time window about said value.

5. The implantable medical device according to claim 4, wherein said calculation unit is configured to: identify the sample corresponding to the maximum value; define a window centered about the maximum value containing a predetermined number of samples; identify the values of the start and end samples of said window, respectively; calculate an average value of said start and end values; and calculate a ratio of said average value and said maximum value as said measure.

6. The implantable medical device according to claim 4, wherein said calculation unit is configured to identify the sample corresponding to the maximum value; define a window centered about the maximum value containing a predetermined number of samples; and calculating an area of said window by adding the values of said predetermined number of samples as said measure.

7. The implantable medical device according to claim 4, wherein said calculation unit is configured to identify the sample corresponding to the maximum value; define a time window centered about the maximum value containing a predetermined number of samples; identify the values of the start and end values of said window, respectively; calculate a first average slope from the sample corresponding to said start value to said sample corresponding to said maximum value; calculate a second average slope from the sample corresponding to the maximum value to the sample corresponding to the end value; and calculate a ratio between said first slope and said second slope as said measure.

8. The implantable medical device according to claim 4, wherein said calculation unit is configured to define a time window at a predetermined amplitude in relation to the maximum value; and calculating a width of said time window as said measure.

9. The implantable medical device according to claim 1, further comprising an analyzer that analyzes said measure to optimize at least one pacing parameter of said pulse generator or to derive a change of a condition of said patient.

10. The implantable medical device according to claim 1, wherein said impedance morphology determining unit determines an averaged impedance morphology curve from said impedance information during a time interval of a plurality of cardiac cycles of said heart.

11. The implantable medical device according to claim 1, wherein said impedance morphology determining unit performs a filtering procedure of said received impedance information and determines an impedance morphology curve from said filtered impedance information.

12. The implantable medical device according to claim 1, wherein said hemodynamic parameter is selected from the group consisting of stroke volume, cardiac output, and contractility.

13. The implantable medical device according to claim 1, further comprising a posture sensor that senses at least one predetermined posture of said patient and that emits at least one posture indicating signal; and wherein said impedance measuring unit initiates a cardiac impedance measuring session upon receiving a posture indicating signal that indicates that said patient is in at least one predetermined posture.

14. The implantable medical device according to claim 1, further comprising a breathing rate that senses a breathing rate of said patient and that emits at least one breathing rate indicating signal; and wherein said impedance measuring unit initiates a cardiac impedance measuring session upon receiving a breathing rate indicating signal that indicates a breathing rate within at least one predetermined interval.

15. The implantable medical device according to claim 1, further comprising an activity level sensor that senses an activity level of said patient and to provide at least one activity level indicating signal; and wherein said impedance measuring unit initiates a cardiac impedance measuring session upon receiving an activity level indicating signal that indicates an activity level within at least one predetermined interval.

16. An implantable medical device as claimed in claim 1 further comprising: a communication unit that receives said output, and an external programmer apparatus that wirelessly communicates with said communication unit.

17. An implantable medical device according to claim 16 comprising a control unit that controls operation of said pulse generator, and, wherein said external programmer apparatus further comprises an analyzer that analyzes said measure to optimize at least one pacing parameter of said pulse generator or to derive a change of a condition of said patient, said external apparatus being communicating said at least one pacing parameter to said control unit.

18. An implantable medical device according to claim 16 comprising a control unit that controls operation of said pulse generator, and, wherein said external programmer apparatus communicates said measure to said control unit and wherein said implantable medical device further comprises an analyzer that analyzes said measure to optimize at least one pacing parameter of said pulse generator or to derive a change of a condition of said patient.

19. A non-transitory computer-readable medium encoded with programming instructions and loadable into a processor of an implantable medical device, said programming instructions causing said implantable medical device to: measure a cardiac impedance of said heart; determine an impedance morphology curve from said impedance information; calculate an extreme point section of said impedance morphology curve and fit a second degree polynomial to the section of the impedance morphology curve in a time window surrounding said extreme point section of said impedance morphology curve; and calculate a measure of a hemodynamic parameter of said heart as a function of a curvature component of the polynomial.

* * * * *